United States Patent
Massonne et al.

(10) Patent No.: US 7,622,617 B2
(45) Date of Patent: Nov. 24, 2009

(54) METHOD FOR PRODUCING α-BISABOLOL FROM FARNESOL

(75) Inventors: Klemens Massonne, Bad Duerkheim (DE); Klaus-Peter Pfaff, Friedelsheim (DE); Juergen Schubert, Dirmstein (DE); Guenther Gottwald, Mannheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 12/092,731

(22) PCT Filed: Oct. 26, 2006

(86) PCT No.: PCT/EP2006/067815

§ 371 (c)(1),
(2), (4) Date: May 6, 2008

(87) PCT Pub. No.: WO2007/051757

PCT Pub. Date: May 10, 2007

(65) Prior Publication Data

US 2008/0269530 A1  Oct. 30, 2008

(30) Foreign Application Priority Data

Nov. 7, 2005 (DE) .................. 10 2005 053 329

(51) Int. Cl.
 *C07C 29/56* (2006.01)
(52) U.S. Cl. ..................................... 568/826
(58) Field of Classification Search .................. 568/826
 See application file for complete search history.

(56) References Cited

FOREIGN PATENT DOCUMENTS

| JP | 60-120828 | 6/1985 |
|---|---|---|
| WO | WO-2004/003301 A1 | 1/2004 |
| WO | WO-2004/033401 A1 | 4/2004 |

OTHER PUBLICATIONS

Fourneron, J-D, et al., "Sur la stéréochimie de la cyclisation du nérolidol en α-bisabolol", Bulletin de la Societe Chimlque de France Masson, 1980, vol. 2, No. 9/10, pp. 387-392.
Fourneron, J-D, et al., "The Stereochemistry of the Cyclization of Nerolidol to α-Bisabolol", Tetrahedron, 1967, vol. 24, No. 2, pp. 859-876, English Translation of CA.
Gutsche, C.D., et al., "Acid-catalyzed Cyclization of Farnesol and Nerolidol", Tetrahedron, 1968, vol. 24, pp. 859-876.

*Primary Examiner*—Sikarl A Witherspoon
(74) *Attorney, Agent, or Firm*—Connolly Bove Lodge & Hutz LLP

(57) ABSTRACT

The present invention relates to a process for preparing α-bisabolol, comprising the reaction of farnesol in the presence of a ketone, of a sulfonic acid and of a further strong acid.

9 Claims, No Drawings

METHOD FOR PRODUCING α-BISABOLOL FROM FARNESOL

TECHNICAL FIELD OF THE INVENTION

The present invention relates to a process for preparing α-bisabolol starting from farnesol.

α-Bisabolol is one of the most important constituents of chamomile oil which is valuable from both a cosmetic and pharmaceutical point of view.

While the synthetic cultivation of medicinal plants is gaining significance owing to an increased demand for "renewable raw materials" and also for natural active ingredients, the restricted natural resources have at the same time led to the search and development of processes for obtaining synthetic products.

Synthetic "alpha-bisabolol" is typically a diastereomeric racemate of equal parts of (+/−)-α-bisabolol and (+/−)-epi-α-bisabolol. All four enantiomers have been found in nature.

Owing to its actions described, there is a constant need for (+)-, (−)- and (+/−)-alpha-bisabolol, and/or (+)-epi-, (−)-epi- and (+/−)-epi-α-bisabolol, i.e. for compounds of the formula (III)

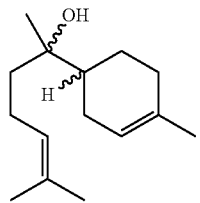

(III)

in which wavy lines each independently represent an S- or R-configuration on the appropriate carbon atom. Thus, a multitude of methods and processes for preparing bisabolol starting from nerolidol have been described in the past.

STATE OF THE ART

In Tetrahedron 24, 8591 (1968), Gutsche et al. describe the acid-catalyzed cyclization of farnesol and nerolidol. Starting from farnesol or nerolidol, the corresponding formates were first obtained by reacting with formic acid and were then hydrolyzed to the alcohols in a second step.

JP 60120828 relates to the use of a nonpolar solvent with a dielectric constant of up to 3.0, specifically hexane, in the aforementioned reaction to improve the workup process and the yield.

WO 2004/03301 discloses a process for preparing α-bisabolol, comprising the reaction of nerolidol with a mixture of a ketone, of a sulfonic acid and perchloric acid. The process is restricted to the nerolidol feedstock and envisages the use of perchloric acid.

OBJECT OF THE INVENTION

It was an object of the present invention to provide a process for the one-stage preparation of α-bisabolol starting from the inexpensive farnesol which is readily available on the industrial scale. The process should be economically advantageous and be performable in a simple manner from a process technology point of view.

DESCRIPTION OF THE INVENTION AND OF THE PREFERRED EMBODIMENTS

The object is surprisingly achieved by the provision of a process for preparing α-bisabolol, comprising the reaction of farnesol in the presence of a ketone, of a sulfonic acid and of a further strong acid.

The present invention relates specifically to processes for preparing α-bisabolol which comprise, as an essential step, the reaction of farnesol in the presence of a mixture of a ketone, of a sulfonic acid and of a further strong acid. Preference is given to performing the inventive reaction of farnesol in a mixture of a ketone, of a sulfonic acid and of a further strong acid.

The starting material used to perform the process according to the invention is farnesol of the formula (IV)

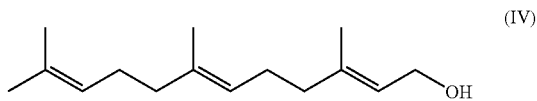

(IV)

which can be used either in pure form or in the form of mixtures of the all-E-isomer of the formula (IV) shown with the corresponding 2- or 6-Z-isomer and/or with 3,7,11-trimethyldodeca-2,4,6,10-tetraen-1-ol of the formula (V)

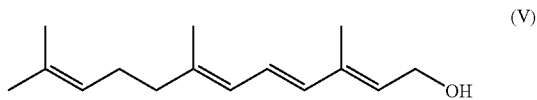

(V)

or its double bond isomers. Preference is given in accordance with the invention to using farnesol with a content of from about 50 to about 100% by weight, preferably from about 70 to about 100% by weight, where said isomers of 3,7,11-trimethyldodeca-2,4,6,10-tetraen-1-ol may preferably be present in an amount of from about 0 to about 30% by weight.

In the inventive reaction, bisabolol of the formula (III) is obtained in the form of racemic mixtures of α-bisabolol of the formula (IIIa)

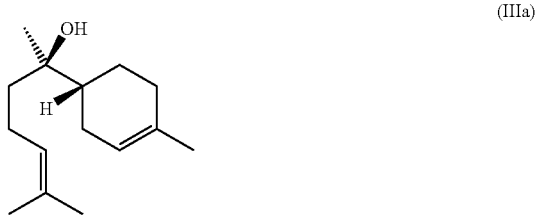

(IIIa)

and epi-α-bisabolol of the formula (IIIb)

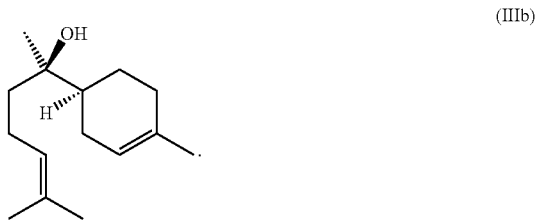

(IIIb)

The process according to the invention is notable in that the reaction of farnesol is carried out in the presence of a ketone, of a sulfonic acid and of a further strong acid.

Ketones preferred in the process according to the invention are those of the formula (I)

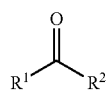
(I)

where the radicals $R^1$ and $R^2$ may be the same or different and are each a straight-chain or branched $C_1$- to $C_4$-alkyl radical, for example methyl, ethyl, n-propyl, n-butyl, isopropyl, sec-butyl or tert-butyl, or else together are a cyclic alkylene radical having from 3 to 5 carbon atoms. Ketones particularly preferred in accordance with the invention include: acetone, methyl ethyl ketone, diethyl ketone and cyclohexanone.

Sulfonic acids preferred in accordance with the invention include those of the formula (II)

(II)

where the radical $R^3$ may be straight-chain or branched $C_1$- to $C_{12}$-alkyl, $C_6$- to $C_{10}$-aryl, $C_7$- to $C_{12}$-alkylaryl or $C_7$- to $C_{12}$-arylalkyl, where the radicals mentioned may each have one or more, generally from 1 to about 6, identical or different substituents which are selected from the group of the substituents fluorine, chlorine, —$OR^4$ and —$C(O)OR^5$, where $R^4$ and $R^5$ are each independently hydrogen or $C_1$- to $C_4$-alkyl.

Examples of radicals preferred for $R^3$ include the following: $C_1$- to $C_{12}$-alkyl as specified above for $C_1$- to $C_4$-alkyl, and additionally n-pentyl, n-hexyl, cyclohexyl, octyl, decyl, dodecyl, trifluoromethyl, 1,1,1-trifluoroethyl, fluoromethyl and difluoromethyl; $C_6$- to $C_{10}$-aryl such as phenyl or naphthyl; $C_7$- to $C_{12}$-alkylaryl, for example para-tolyl, ortho-tolyl, para-tert-butylphenyl; $C_7$- to $C_{12}$-arylalkyl such as benzyl, phenylethyl.

Sulfonic acids of the formula (II) which are particularly preferred in the process according to the invention include: methanesulfonic acid, trifluoromethanesulfonic acid, benzenesulfonic acid, p-toluenesulfonic acid and naphtholsulfonic acid.

The molar ratio of ketone to the farnesol to be converted can be varied within wide ranges, but is preferably in the range from 0.1:1 to 30:1. Molar ratios in the range from about 1:1 to about 15:1, more preferably from about 5:1 to about 10:1, have been found to be particularly useful.

The molar ratio of sulfonic acid to the farnesol to be converted can also be varied within a wide range. However, preference is given to molar ratios in the range from 0.001:1 and 10:1, particularly good results having been achieved with molar ratios in the range from 0.01:1 to 0.5:1.

The inventive reaction of farnesol to give bisabolol is carried out, in addition to the ketone mentioned and the sulfonic acid mentioned, in the presence of at least one further strong acid, i.e. either in the presence of a strong acid or of a mixture of different strong acids. In the context of the present invention, the term strong acid is preferably understood to mean an acid which has a pKa of up to about 2, preferably of from about −3 to about 2 and more preferably from about −3 to about 0.

Strong acids particularly preferred in accordance with the invention include: sulfuric acid, perchloric acid, tetrafluoroboric acid, trifluoromethanesulfonic acid, trichloroacetic acid, trifluoroacetic acid, nitric acid, phosphoric acid, pyrophosphoric acid and hexafluorophosphoric acid, most preferably tetrafluoroboric acid ($HBF_4$), perchloric acid and sulfuric acid, and especially preferably tetrafluoroboric acid and sulfuric acid.

The further strong acid to be used in accordance with the invention is preferably used in amounts of from about 0.1 to about 100 mol %, more preferably from about 2 to about 40 mol % and especially preferably in an amount of from about 10 to about 30 mol %, based on the amount of farnesol to be converted.

The inventive reaction can be carried out in the presence of water, in which case the amount of water present is tolerable within certain limits. In some cases, the presence of water has even been found to be advantageous, in which case the molar ratio between water and farnesol should be from about 0.001:1 to about 10:1, preferably from about 0.01:1 to about 1:1.

The inventive reaction is appropriately carried out at temperatures of from about −10° C. to about 50° C., preferably from about 10° C. to about 30° C. Typically, the inventive reaction is substantially complete after reaction times of from about 2 h to about 3 days, often after about 24 h, depending on the selected reaction conditions. The workup of the product mixtures obtained in accordance with the invention can be undertaken by methods known to those skilled in the art. Typically, the reaction mixture is first neutralized and then worked up by extraction. For further purification or separation of the components present in the crude product, further purification processes, for example distillations, may be undertaken.

The reaction mechanism of the inventive reaction is currently unexplained, but appears to differ from the reaction mechanism detailed in WO 2004/03301, in which farnesol is formed as a by-product in the conversion of nerolidol to bisabolol.

The process according to the invention leads advantageously in one step directly from farnesol to the desired bisabolol of the formula (III), and thus constitutes a substantial improvement in comparison to the known multistage processes. In addition, it can be carried out in a simple manner in process technology terms at unproblematic reaction temperatures and pressures.

The process according to the invention is notable in that it leads to particularly pure bisabolol. It is possible by virtue of the process according to the invention to keep the content of unconverted farnesol in the product mixture below 2% by weight, which constitutes a considerable advantage with regard to the further purification or utilization of the bisabolol obtained in accordance with the invention.

Especially in the case of distillative removal of farnesols, depending upon the selected distillation conditions, there is often considerable thermal stress on the bisabolol present in the product mixture, which can entail undesired side reactions or decomposition reactions.

Starting from farnesol, the process according to the invention leads in one stage to a product mixture which comprises α-bisabolol in a particularly high content and additionally only small amounts of unconverted farnesol. It thus constitutes a distinct improvement to the known two-stage processes for preparing α-bisabolol starting from farnesol. The distillative removal of the remaining amount of farnesol therefore does not take a long time, which has the ultimate result that bisabolol can be prepared in good space-time yields, in high purity and with a sensorily advantageous quality when the process according to the invention is used.

The present invention additionally also relates to the use of sulfonic acids as catalysts or reactants or reagents for preparing α-bisabolol starting from farnesol.

The examples which follow serve to illustrate the process according to the invention without restricting it in any way whatsoever:

EXAMPLE 1

GC Separation Conditions:
Column: 30 m DB_WAX; internal diameter 0.25 mm; film thickness: 0.25 μm
Carrier gas: helium, 1 ml/min
Injection block temperature 200° C.
Temperature program: 160 to 190° C. at 2° C./min; 190 to 240° C. at 5° C./min; then isothermal at 240° C. for 10 min.

A standard apparatus consisting of a 2 l three-neck flask with reflux condenser, dropping funnel and thermometer was initially charged with 132 g of farnesol with a content of 81% by weight (in addition to 19% by weight of high boilers) with 348 g of acetone, and cooled to 15° C. Within 10 min, a mixture of 16.2 g of methanesulfonic acid and 5.4 g of perchloric acid (60%) was then added at 15° C. and the mixture was then stirred at 20° C. for 10 h.

For workup, the mixture obtained was admixed with 300 ml of water, brought to pH 7 with sodium hydrogencarbonate and extracted with 300 ml of ether. Distillative removal of the ether afforded 121 g of a product mixture which was analyzed by gas chromatography and had (in addition to unidentified by-products) the following constituents (fractions in GC area %): bisabolene: 31.6%, nerolidol: 4%, bisabolol: 37.5%, farnesol 1.2%.

The invention claimed is:

1. A process for preparing α-bisabolol, comprising reacting farnesol in the presence of a ketone, a sulfonic acid, and an additional strong acid.

2. The process of claim 1, wherein said ketone is of formula (I)

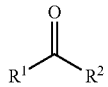

wherein
R$^1$ and R$^2$
are, identically or differently a straight-chain or branched C$_1$- to C$_4$-alkyl radical or together define a cyclic alkylene radical having from 3 to 5 carbon atoms.

3. The process of claim 1, wherein said sulfonic acid is of formula (II)

wherein
R$^3$ is straight-chain or branched C$_1$- to C$_{12}$-alkyl, C$_6$- to C$_{10}$-aryl, C$_7$- to C$_{12}$-alkylaryl or C$_7$- to C$_{12}$-arylalkyl, each of which is optionally substituted with one or more substituents selected from the group consisting of fluorine, chlorine, —OR$^4$, and —C(O)OR$^5$, wherein R$^4$ and R$^5$ are each independently hydrogen or C$_1$- to C$_4$-alkyl.

4. The process of claim 1, wherein said sulfonic acid and/or said additional strong acid has a pKa value of up to 2.

5. The process according to claim 1, wherein said additional strong acid is selected from the group consisting of sulfuric acid, perchloric acid, tetrafluoroboric acid, trifluoromethanesulfonic acid, trichloroacetic acid, trifluoroacetic acid, nitric acid, phosphoric acid, pyrophosphoric acid, and hexafluorophosphoric acid.

6. The process of claim 1, wherein the amount of said additional strong acid is from 0.1 to 100 mol % based on the amount of farnesol.

7. The process of claim 1, wherein said farnesol is a mixture of the all-E-isomer of the formula (IV)

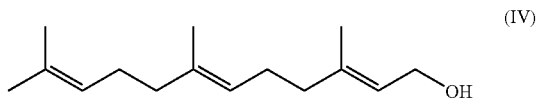

with the corresponding 2- or 6-Z-isomer, and/or with 3,7,11-trimethyldodeca-2,4,6,10-tetraen-1-ol of the formula (V)

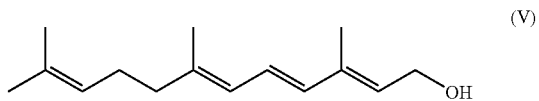

or its double bond isomers.

8. The process of claim 1, wherein the molar ratio of ketone to farnesol is in the range of from 0.1:1 to 30:1.

9. The process of claim 1, wherein the molar ratio of sulfonic acid to farnesol is in the range of from 0.001:1 to 10:1.

* * * * *